United States Patent
Ischinger et al.

(10) Patent No.: US 9,254,208 B2
(45) Date of Patent: Feb. 9, 2016

(54) OBLIQUE STENT

(71) Applicant: Thomas Ischinger, Munich (DE)

(72) Inventors: Thomas Ischinger, Munich (DE); Ronald Jay Solar, San Diego, CA (US); Glen Lieber, Poway, CA (US)

(73) Assignee: Thomas Ischinger, Munich (DE)

( * ) Notice: Subject to any disclaimer, the term of this patent is extended or adjusted under 35 U.S.C. 154(b) by 315 days.

(21) Appl. No.: 13/826,399

(22) Filed: Mar. 14, 2013

(65) Prior Publication Data

US 2014/0277377 A1   Sep. 18, 2014

(51) Int. Cl.
*A61F 2/915* (2013.01)
*A61F 2/82* (2013.01)

(52) U.S. Cl.
CPC ........... *A61F 2/915* (2013.01); *A61F 2002/821* (2013.01); *A61F 2002/91558* (2013.01); *A61F 2230/0008* (2013.01); *A61F 2250/0026* (2013.01)

(58) Field of Classification Search
CPC . A61F 2/915; A61F 2002/91558; A61F 2/89; A61F 2002/9155; A61F 2/86; A61F 2002/91508; A61F 2002/91533; A61F 2002/91525; A61F 2002/91516; A61F 2002/91541
See application file for complete search history.

(56) References Cited

U.S. PATENT DOCUMENTS

| | | |
|---|---|---|
| 5,520,647 A | 5/1996 | Solar |
| 5,569,199 A | 10/1996 | Solar |
| 5,893,887 A | 4/1999 | Jayaraman |
| 6,491,719 B1 | 12/2002 | Fogarty et al. |
| 6,682,556 B1 | 1/2004 | Ischinger |
| 2001/0016767 A1 | 8/2001 | Wilson et al. |
| 2003/0050688 A1 | 3/2003 | Fischell et al. |
| 2004/0186560 A1 | 9/2004 | Alt |
| 2005/0113686 A1 | 5/2005 | Peckham |
| 2005/0154447 A1 | 7/2005 | Goshgarian |
| 2005/0222672 A1 | 10/2005 | Shmulevitz |
| 2007/0021816 A1 | 1/2007 | Rudin |
| 2008/0051868 A1* | 2/2008 | Cottone ............... A61F 2/91 623/1.11 |
| 2009/0171426 A1 | 7/2009 | Magnuson |
| 2010/0070014 A1 | 3/2010 | Viller |
| 2010/0094405 A1* | 4/2010 | Cottone ............... A61F 2/91 623/1.16 |

FOREIGN PATENT DOCUMENTS

| | | |
|---|---|---|
| WO | 0057813 | 10/2000 |
| WO | 2009140719 | 11/2009 |
| WO | 2012062144 | 5/2012 |

* cited by examiner

*Primary Examiner* — Katherine M Shi
*Assistant Examiner* — Michael Mendoza
(74) *Attorney, Agent, or Firm* — Daniel J. Swirsky; Ricki L. Simon; AlphaPatent Associates Ltd.

(57) ABSTRACT

A stent having a main body with a proximal end and a distal end section having proximal and distal openings used for treatment of lesions in blood vessels and hollow organs, particularly at the ostium of side branches. The stent adapts to the anatomical configuration of a vessel branch by having at least one oblique end section in at least its expanded state. Truncated versions of the oblique end section are described as well.

11 Claims, 11 Drawing Sheets

OBLIQUE STENT

FIELD OF THE INVENTION

The present invention is directed to a stent used to treat a bifurcation. More specifically, the present invention is directed to an oblique stent wherein in an expanded state, at least one end of the stent is at an angle to a plane which is perpendicular to a longitudinal axis of the stent.

BACKGROUND OF THE INVENTION

Stents are prostheses which may be made out of metal and may be either balloon expandable or self expandable, or which may be made out of a polymer. Stents are used for scaffolding or dilatation of diseased segments in hollow organs, particularly in blood vessels, which may be applied by use of catheter techniques, as used in heart catheterization and angioplasty procedures. Stents are made of wire-like materials or cut from tubes by laser cutting techniques or other techniques such as etching. The wire-like mesh forming the tubular wall of the stents includes struts (stent material) and gaps between the struts (no material). The struts usually exhibit an alternation of sinus wave shapes in circumferential extension and sinus wave shapes in longitudinal extension, or a diamond shaped configuration, or a combination of different shapes.

If a lesion is located in or near a bifurcation of a vessel, i.e. at the origin of a side branch taking off from a main branch, a balloon angioplasty procedure may be performed and a stent may be placed after the dilatation in the dilated segment in order to maintain acute and late vessel patency by scaffolding the dilated segment either permanently or over a period of time (e.g. via use of a bioabsorbable stent). The stent may be further coated with a drug for inhibition of restenosis development. The stent may also be placed as primary treatment without prior balloon dilatation or catheter based pre-treatment methods. The stent must cover the target lesion completely, and in some cases should even reach beyond the diseased segment into the adjacent non-diseased or less diseased vessel areas, in order to fully use the potential of the stent for acute and late vessel patency. Thus, in the case of a bifurcation, the stent must cover the ostium of the side branch. The ostium of a side branch often has a cross-sectional plane which does not run perpendicular to the longitudinal axis of the side branch, as the side branch may take off at an angle other than 90°, such as at an angle between 40°-60°. Conventional stents may not adequately provide coverage in such circumstances.

Various solutions for bifurcation or ostial stents and catheters for delivery of such stents have been disclosed. US Patent Publication 20050222672 to Shmulevitz discloses a self expandable stent, covered with a retractable sheath for compression of the stent, with a stem portion and a cap portion. The stent has flared ends and a toroidal shape for introduction into the main branch, and for overlapping the carina of the vessel branching area into the side branch.

Similarly, US Patent Publication 20050154447 to Goshgarian discloses a self expandable stent with flared ends. A dual balloon implantation method is used to implant the balloon expandable stent into an ostium. In order to increase the diameter of the ostial opening of the stent, i.e. to flare the ostial stent portion, one balloon of the dual balloon system is used.

The above-referenced disclosures fail to disclose using a single stent that fits the bifurcation anatomy without protrusion of a portion of the stent from the side branch into the main branch or from the main branch into the side branch. Rather, they disclose protrusion portions and/or the use of stent assemblies or multiple stents combined.

Moreover, if two stents are needed for treatment of a lesion in the main branch, with the necessity of bridging the ostium of the side branch, the protruding portions of the stents may lead to metal overlap, collision and stent strut distortion. This may reduce the acute and late (long term) chances of procedural success, as well as lead to immediate complications, such as an increased risk for thrombosis in the stents.

U.S. Pat. No. 6,682,556 to Ischinger discloses a catheter for placement of an oblique stent into a side branch. However, Ischinger does not disclose a specific design of an oblique stent which can be used to meet the requirements of successful bifurcation stent treatment.

There is thus a need for a stent which upon expansion has at least one oblique end, wherein the stent design and architecture are suitable for providing such oblique end, and wherein the stent may be successfully used to treat a bifurcated vessel.

SUMMARY OF THE INVENTION

There is provided, in accordance with embodiments of the present invention, a tubular stent having a first end, a second end, a longitudinal axis extending from the first end to the second end, and an expandable stent wall extending from the first end to the second end along the longitudinal axis, wherein upon expansion of the tubular stent, the first end is configured at an oblique angle to a plane which is perpendicular to the longitudinal axis.

In accordance with further features in embodiments of the invention, the second end of the stent may be parallel to or at an oblique angle to a plane which is perpendicular to the longitudinal axis. The first and/or second end may be a truncated oblique end. This may be formed by the first end having a portion which is cut at an angle to a plane which is perpendicular to the longitudinal axis, and further including a truncated portion which is cut parallel to a plane which is perpendicular to the longitudinal axis. Alternatively or in addition, this may be formed by the expandable stent wall having an architecture which, in an unexpanded configuration is non-oblique, and in an expanded configuration includes at least one oblique end. The expandable stent wall includes a top portion and a bottom portion, and may include a configuration wherein upon expansion of the expandable stent wall, the top portion is longer than the bottom portion or vice versa.

In accordance with further features in embodiments of the invention, the expandable stent wall may be comprised of multiple adjacent circumferential rings, wherein each of the circumferential rings is arranged at an oblique angle to a plane which is perpendicular to the longitudinal axis. In some embodiments, the expandable stent wall includes a body portion having body portion strut elements and an end section having end section strut elements, wherein the end section strut elements have a different configuration than the body portion strut elements. In some embodiments, the body portion strut elements are circumferentially arranged axially sinusoidal strut elements having proximal and distal peaks in a direction of the longitudinal axis, and the axially sinusoidal strut elements form neighboring circumferential rings. Circumferential rings may be connected to each other via connecting elements attaching distal peaks of a first circumferential ring to proximal peaks of a second circumferential ring.

In embodiments of the present invention, the end section may include a triangular central element having a proximal end with a first leg and a second leg, and a distal end having an apex, a first longitudinally sinusoidal strut element positioned above the triangular central element having proximal end and a distal end, a second longitudinally sinusoidal strut element positioned below the triangular central element having a proximal end and a distal end, and a straight strut element positioned distal to the triangular central element and having a straight strut element proximal end and distal end, wherein the first leg and second leg of the triangular central element proximal end are connected to the body portion strut elements and the triangular central element distal end is connected to the straight strut element proximal end, and wherein the first and second longitudinally sinusoidal strut element proximal ends are connected to the body portion strut elements, and the first and second longitudinally sinusoidal strut element distal ends are connected to the straight strut element distal end.

In embodiments of the present invention, the end section includes a first longitudinally sinusoidal outer edge strut, a second longitudinally sinusoidal outer edge strut, an axially sinusoidal element having sinusoidal element proximal peaks and sinusoidal element distal peaks, and sandwiched between the first and second longitudinally sinusoidal outer edge struts, and a terminal axially sinusoidal end piece. The terminal axially sinusoidal end piece includes multiple sinusoidal portions having a shorter amplitude than an amplitude of the axially sinusoidal elements, terminal end piece distal peaks and terminal end piece proximal peaks on the multiple sinusoidal portions and an end piece top left leg and an end piece bottom left leg, wherein the sinusoidal element distal peaks are connected to the terminal end piece proximal peaks, and wherein the first longitudinally sinusoidal outer edge element is connected to the end piece top left leg and the second longitudinally sinusoidal outer edge element is connected to the end piece bottom left leg.

In accordance with further features in embodiments of the invention, the stent wall may have a bottom portion having a first strut configuration and a top portion having a second strut configuration. In some embodiments, the bottom portion includes a longitudinal contracting strut configuration having a bottom portion first length in an unexpanded state and a bottom portion second length upon expansion of the tubular stent, wherein the bottom portion second length is shorter than the bottom portion first length due to the longitudinal contracting strut configuration, and wherein the top portion includes a longitudinal length-maintaining strut configuration, wherein the top portion has a top portion first length in an unexpanded state and a top portion second length upon expansion of the tubular stent, wherein the top portion second length is substantially the same as the top portion first length due to the longitudinal length-maintaining strut configuration.

Unless otherwise defined, all technical and scientific terms used herein have the same meaning as commonly understood by one of ordinary skill in the art to which this invention belongs. Although methods and materials similar or equivalent to those described herein can be used in the practice or testing of the embodiments of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of various embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several embodiments of the invention may be embodied in practice.

In the drawings.

Figure 1A:
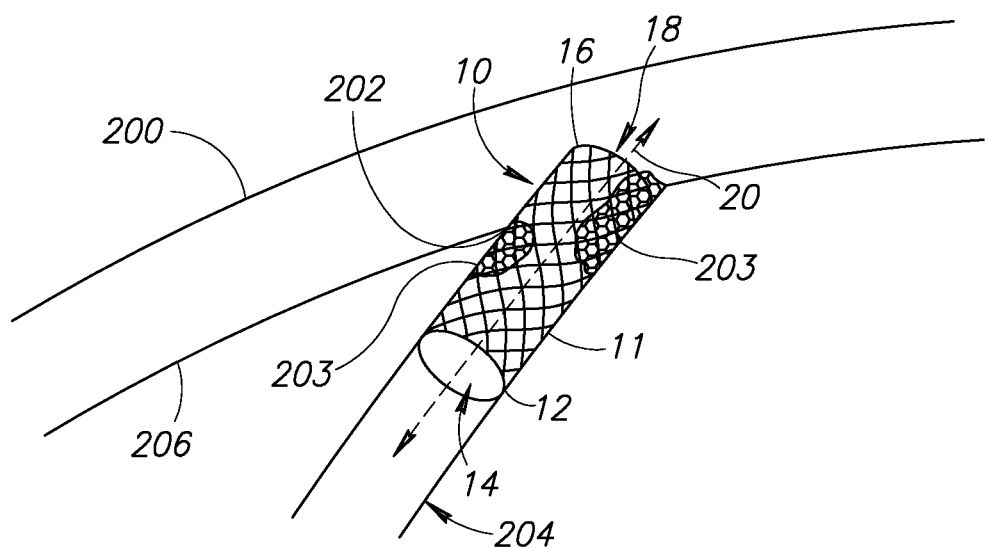
FIGS. 1A and 1B are schematic illustrations of a non-oblique stent positioned at a bifurcation in a vessel.

It will be appreciated that for simplicity and clarity of illustration, elements shown in the drawings have not necessarily been drawn accurately or to scale. For example, the dimensions of some of the elements may be exaggerated relative to other elements for clarity or several physical components may be included in one functional block or element. Further, where considered appropriate, reference numerals may be repeated among the drawings to indicate corresponding or analogous elements. Moreover, some of the blocks depicted in the drawings may be combined into a single function.

DETAILED DESCRIPTION OF THE INVENTION

In the following detailed description, numerous specific details are set forth in order to provide a thorough understanding of the present invention. It will be understood by those of ordinary skill in the art that embodiments of the present invention may be practiced without these specific details. In other instances, well-known methods, procedures, components and structures may not have been described in detail so as not to obscure the present invention.

The present invention relates to a stent which has at least one oblique end in its expanded state. Further advantages of the design of the catheter of the present invention will be described herein below.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein are for the purpose of description and should not be regarded as limiting.

Figure 1B:
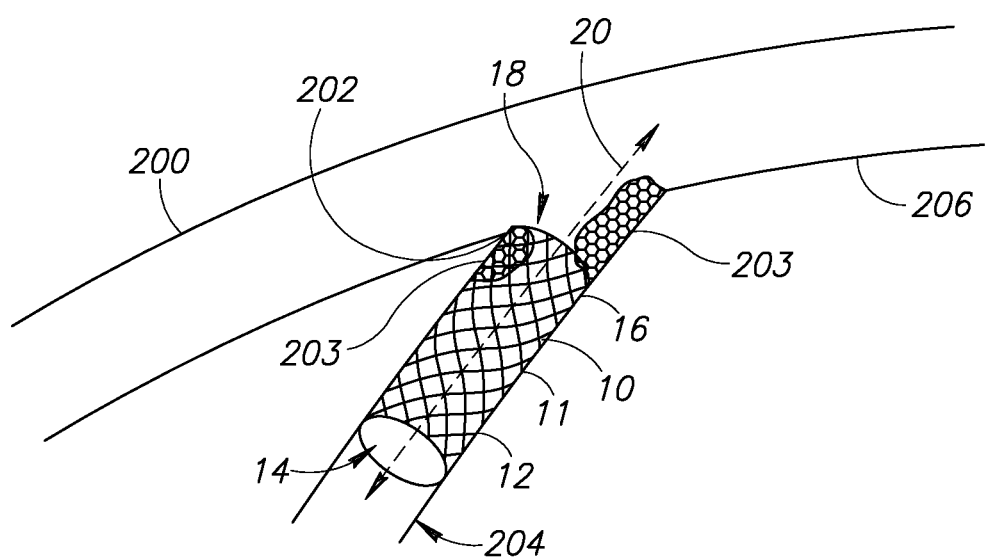

Reference is now made to FIGS. 1A and 1B, which are schematic illustrations of a non-oblique stent 10 positioned at a bifurcation 202 in a vessel 200. A lesion 203 is shown in a side branch 204 of vessel 200. Non-oblique stent 10 is comprised of a tubular or sleeve-like stent body 11 with a distal end 12 having a distal end opening 14, and a proximal end 16 having a proximal end opening 18. Stent body 11 runs from proximal end 16 to distal end 12 along a longitudinal axis 20. The stent body 11 is generally comprised of metallic or non-metallic materials, such as stainless steel, for example, which are plastically deformable by balloon expansion or by other expansion means. In some configurations, the stent body 11 is comprised of self-expanding plastically and/or elastically deformable materials such as Nitinol™. Stent 10 can be cut by laser techniques from a tube, or can be made from wire-like materials which are bent into a specific configuration and attached to one another radially and longitudinally. Such methods are known in the art.

Both distal end 12 and proximal end 16 of non-oblique stent 10 are cut in a plane which runs perpendicular to longitudinal axis 20. As shown in FIG. 1A, when non-oblique stent 10 is placed in a side branch 204 of vessel 200 at bifurcation 202, proximal end 16 may protrude into a main branch 206 of vessel 200. This may prevent advancement of catheters through main branch 206 beyond the protruding stent. Moreover, if a stent is needed for treatment of a lesion in main branch 206 with the need to bridge the ostium of side branch 204, the protruding portion of the stent in side branch 204 will lead to metal overlap and collision, and stent strut distortion, which may reduce the acute and late (long term) chances of procedural success significantly, or which can lead to complications and pose an increased risk for thrombosis in the stents.

As shown in FIG. 1B, if protrusion of non-oblique stent 10 into main branch 206 is avoided by placement of non-oblique stent 10 in side branch 204 only, then a portion of side branch 204 will remain uncovered.

Figure 2A:
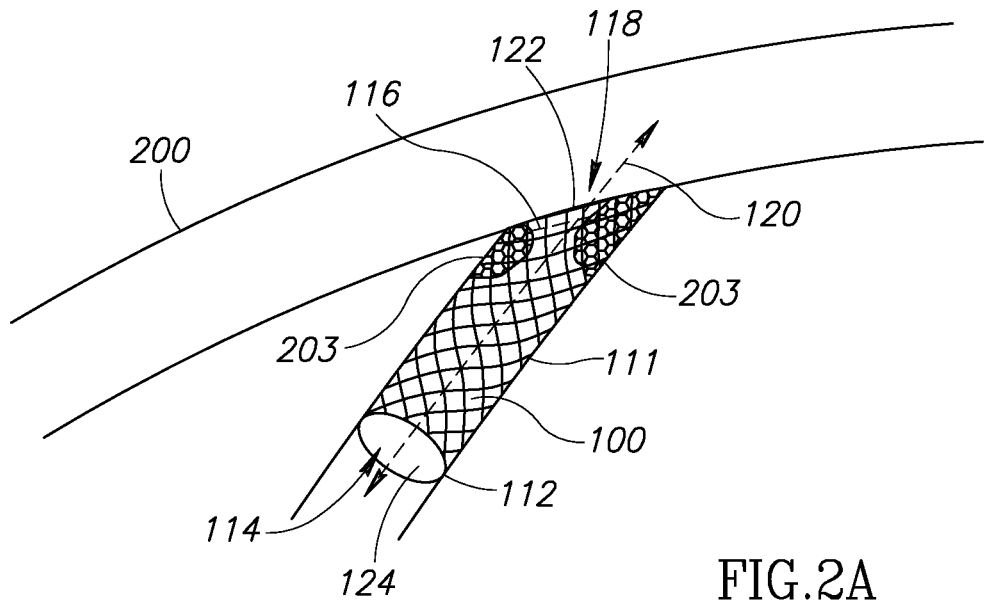
FIGS. 2A-2D are schematic illustrations of an oblique stent positioned in branches of a bifurcated vessel.
Figure 2B:
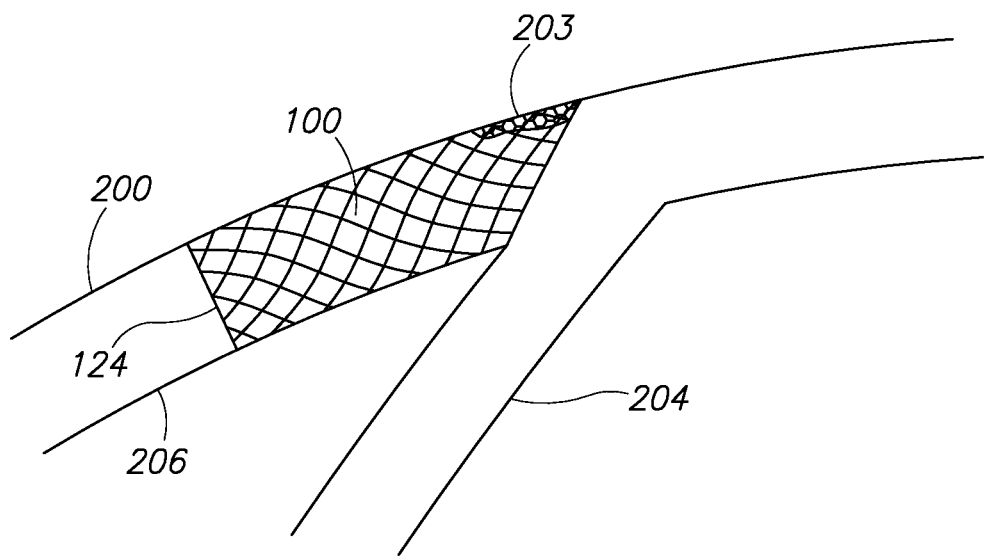
Figure 2C:
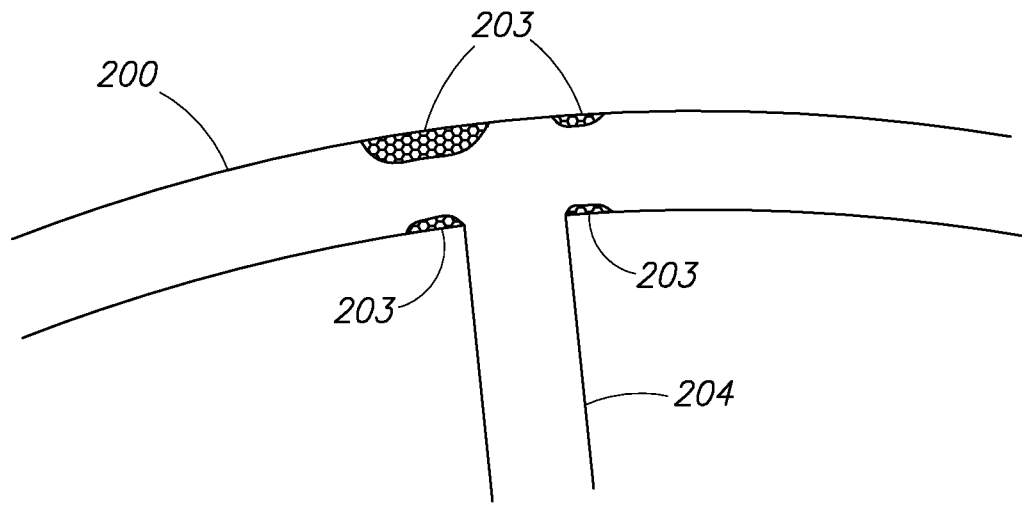
Figure 2D:
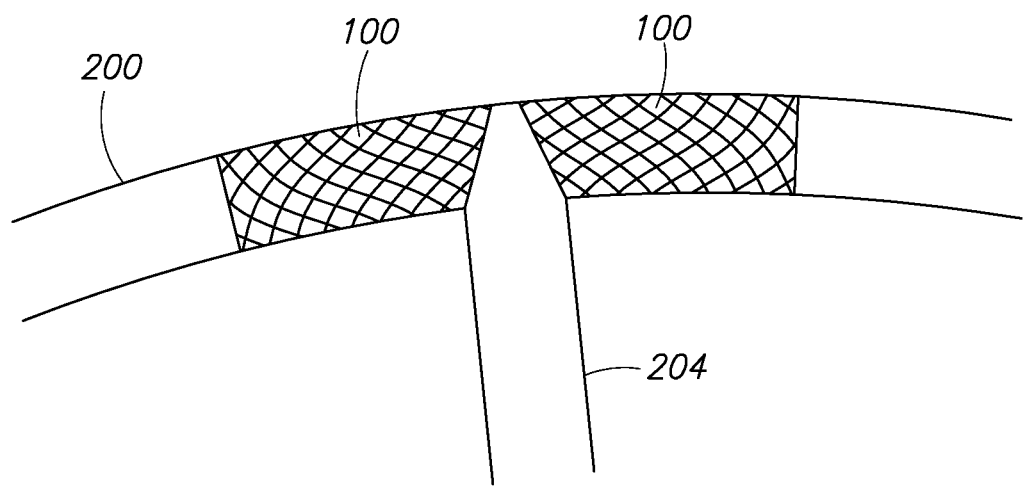

Reference is now made to FIGS. 2A-2D, which are schematic illustrations of an oblique stent 100 positioned in branches of vessel 200. Oblique stent 100 comprises a tubular or sleeve-like stent body 111 with a distal end 112 having a distal end opening 114, and a proximal end 116 having a proximal end opening 118. Stent body 111 runs from proximal end 116 to distal end 112 along a longitudinal axis 120. At least one of distal end 112 and proximal end 116 of oblique stent 100 is cut at an angle to a plane which runs perpendicular to longitudinal axis 120 and is referred to as oblique end 122. The angle may be in a range of 0-90 degrees, and in some embodiments may be in a range of 40-60 degrees. One of proximal end 116 and distal end 112 of oblique stent 100 may be cut in a plane which is perpendicular to longitudinal axis 120. This configuration at an end of a stent is referred to herein as a perpendicular end 124. As shown in FIG. 2A, lesion 203 is located in side branch 204, and oblique stent 100 may be positioned in side branch 204. As shown in FIG. 2B, lesion 203 is located in main branch 206, and oblique stent 100 may be positioned in main branch 206. As shown in FIGS. 2C and 2D, multiple lesions 203 are located in main branch 206 in an area surrounding an ostium of side branch 204 (as depicted in FIG. 2C), and multiple oblique stents 100 may be positioned in main branch 206 at an area surrounding bifurcation 202 (as depicted in FIG. 2D). Thus, as shown in FIGS. 2A-2D, the oblique design of oblique end 122 may be used to better manage stent placement into side branch 204 and/or into main branch 206 at bifurcation 202.

Although such stents have been disclosed in concept, the specific architecture required for producing oblique stent 100 and for minimizing the risk of protrusion into main branch 206 from side branch 204 or vice versa has not been disclosed. Moreover, the architecture must provide sufficient radial support at oblique end 122 after dilatation of oblique stent 100.

Figure 3A:
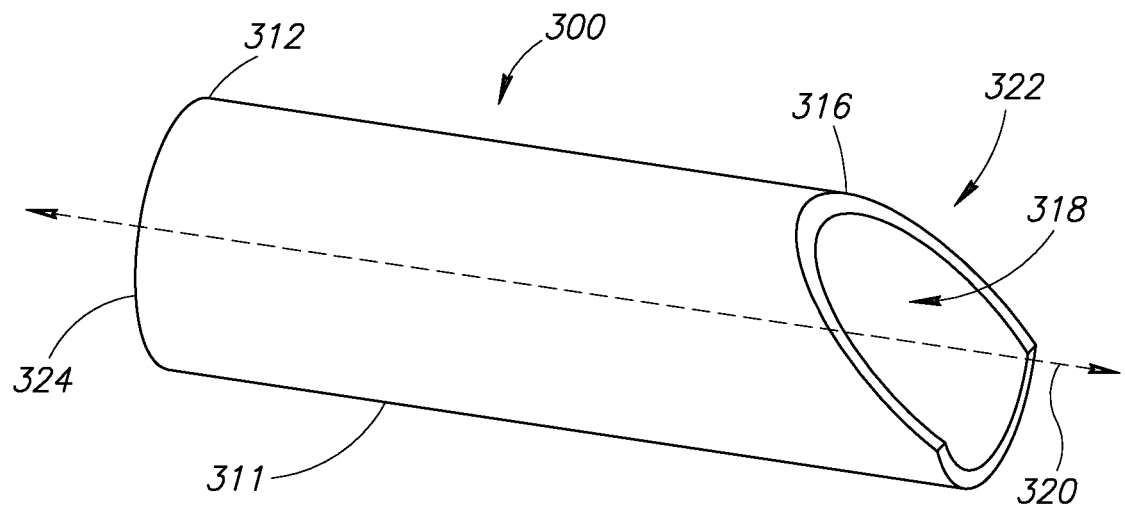
FIGS. 3A and 3B are perspective illustrations of a truncated oblique stent, shown from two different viewing angles, in accordance with embodiments of the present invention.
Figure 3B:
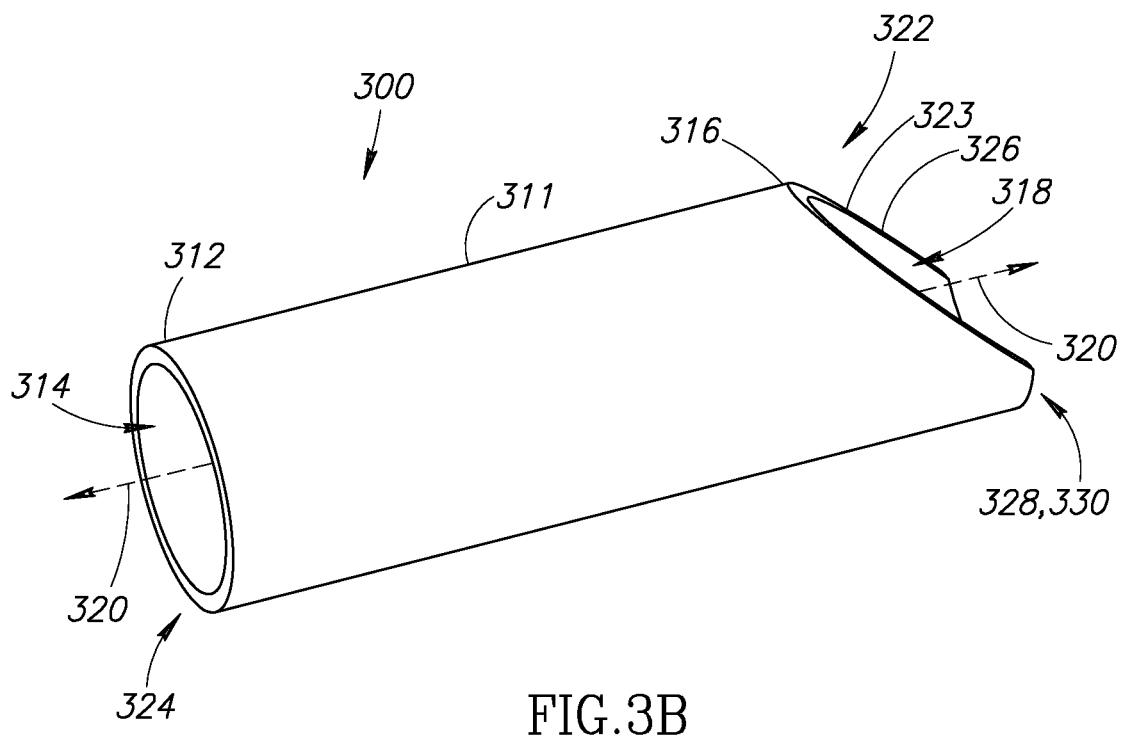

Reference is now made to FIGS. 3A and 3B, which are perspective illustrations of a truncated oblique stent 300, shown from two different viewing angles, in accordance with embodiments of the present invention. Truncated oblique stent 300 is designed to provide additional support at an oblique end of the stent. Truncated oblique stent 300 includes a proximal end 312 having a proximal end opening 314, a distal end 316 having a distal end opening 318 and a stent body 311 extending from proximal end 312 to distal end 316 along a longitudinal axis 320. {Proximal opening 314 has a substantially circular or ovoid shape, in accordance with the cylindrical configuration of stent body 311. Proximal opening 314 is cut in a plane which is perpendicular to longitudinal axis 320. This configuration at an end of a stent is referred to herein as perpendicular end 324. Distal end 316 of truncated oblique stent 300 is partially cut at an angle to a plane which runs perpendicular to longitudinal axis 320 and is referred to as oblique end 322. Oblique end 322 includes a first distal opening portion 326 and a second distal opening portion 328, wherein first distal opening portion 326 is cut an oblique angle to a plane which is perpendicular to longitudinal axis 320, and second distal opening portion 328 is cut in a plane which is perpendicular to longitudinal axis 320. Thus, second distal opening portion 328 may be described as a truncated portion 330 of oblique end 322. This configuration at an end of a stent is referred to herein as an oblique truncated end 323. In some embodiments, proximal end 312 is an oblique truncated end, while distal end 316 is a perpendicular end. In yet other embodiments, both proximal end 312 and distal end 316 are oblique truncated ends.

Figure 4:
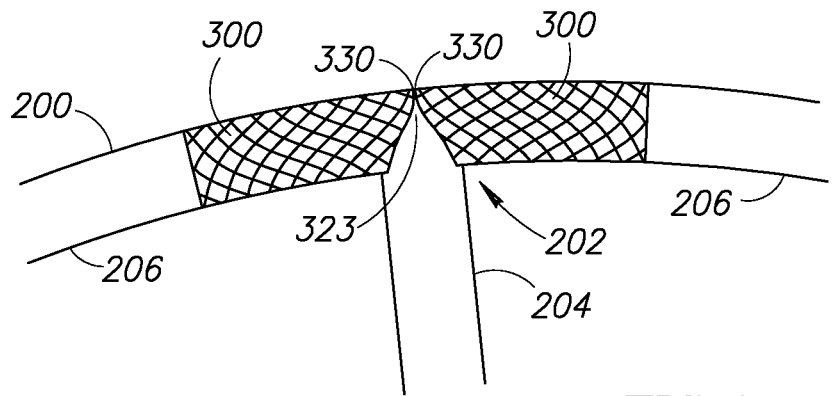
FIG. 4 is a schematic illustration of two truncated oblique stents positioned in a main branch of a bifurcated vessel in an area around a bifurcation, in accordance with embodiments of the present invention.

Reference is now made to FIG. 4, which is a schematic illustration of two truncated oblique stents 300 positioned in a main branch 206 of a bifurcated vessel 200 in an area around a bifurcation 202, in accordance with embodiments of the present invention. Truncated portions 330 are depicted facing each other within main branch 206 such that both main branch 206 and side branch 204 are open to flow of blood.

Figure 5A:
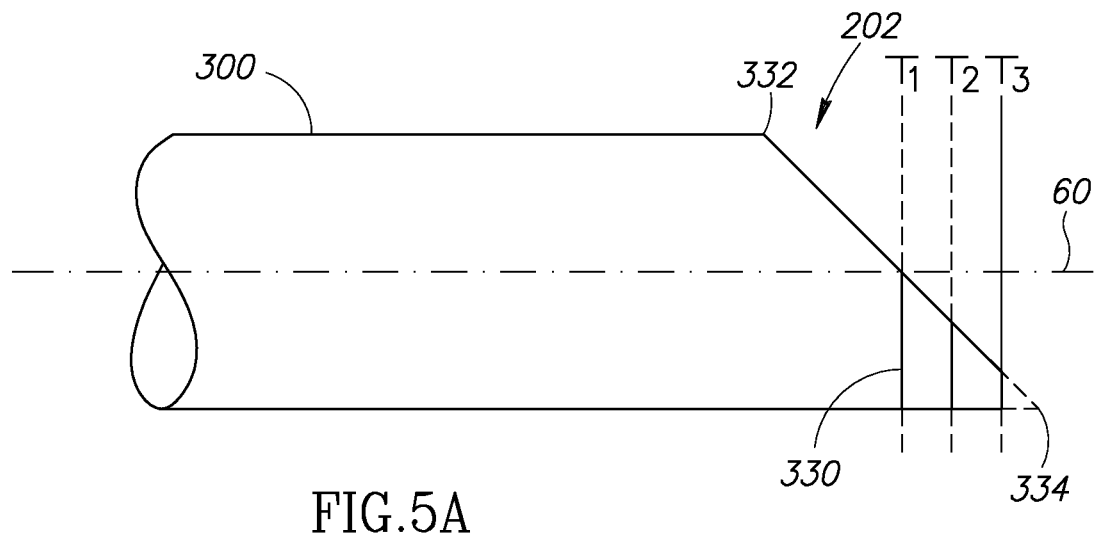
FIG. 5A and FIG. 5B are schematic illustrations of a truncated oblique stent in accordance with embodiments of the present invention.
Figure 5B:
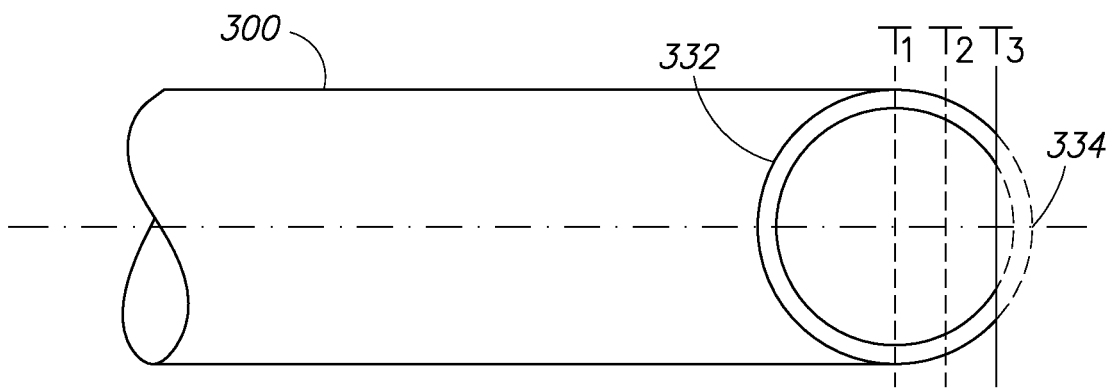

Reference is now made to FIG. 5A and FIG. 5B, which are schematic illustrations of truncated oblique stent 300 in accordance with embodiments of the present invention. As depicted in FIGS. 5A and 5B, oblique end 322 includes a short edge 332 and a long edge 334. Truncated portion 330 may be positioned at varying distances from long edge 334, as depicted by cutting planes $T_1$, $T_2$ and $T_3$. As seen more clearly in FIG. 5B, the closer truncated portion 330 is to short edge 332, the larger the circumference of truncated portion 330.

In one embodiment, truncated oblique stent 300 may be constructed by cutting a non-oblique stent 10 at one or both ends so as to form one or two truncated oblique ends. This may be done in an unexpanded or partially unexpanded state wherein the truncated oblique end configuration is maintained during and after stent expansion. Alternatively, this may be done in an expanded or partially expanded state, wherein the truncated oblique end configuration is maintained when compressed or crimped onto a balloon. In additional embodiments, truncated oblique stent 300 may be constructed by having a specific stent architecture which converts at least one perpendicular end of the stent into a truncated oblique end upon expansion of stent 300, as will be described in further detail hereinbelow.

Figure 6A:
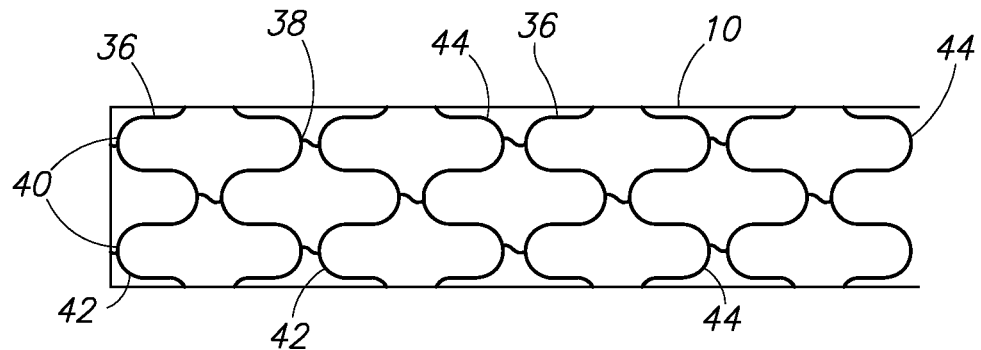
FIGS. 6A-6C are plan view illustrations of a non-oblique stent, showing a stent wall architecture in different configurations.
Figure 6B:
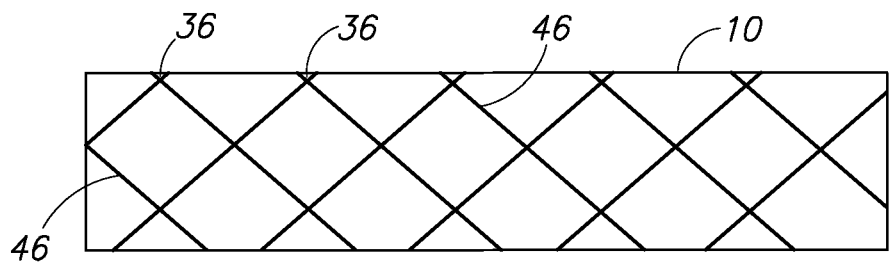
Figure 6C:
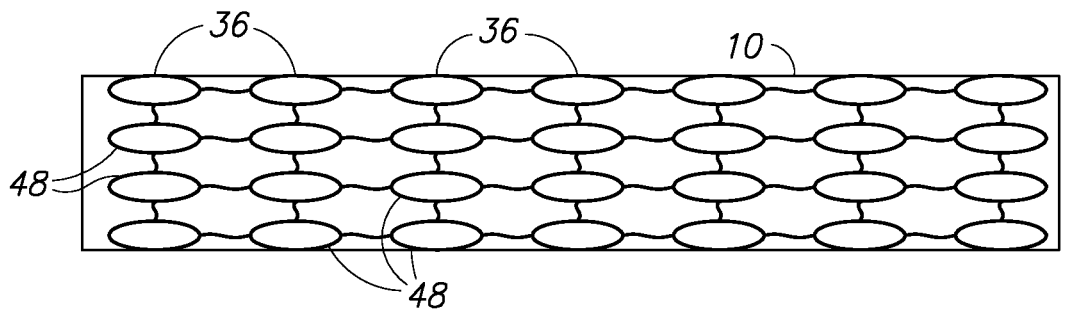

Reference is now made to FIGS. 6A-6C, which are plan view illustrations of a non-oblique stent 10, showing a stent wall architecture in different configurations. As shown in FIG. 6A, non-oblique stent 10 is comprised of multiple adjacent circumferential rings 36, wherein each of circumferential rings 36 is connected to another of circumferential rings 36 by connecting elements 38. In the embodiment shown in FIG. 6A, circumferential rings 36 are comprised of axially sinusoidal strut elements 40. Each of axially sinusoidal strut elements 40 has a series of alternating proximal peaks 42 and distal peaks 44. Connecting elements 38 connect, for example, a distal peak 44 of a first circumferential ring 36 with a proximal peak 42 of another circumferential ring 36. In the embodiment shown in FIG. 6B, circumferential rings 36 are comprised of diamond shaped struts 46. In the embodiment shown in FIG. 6C, circumferential rings 36 are comprised of elliptical shaped struts 48. It should be readily apparent that circumferential rings 36 may have any configuration suitable for a stent wall.

Figure 7A:
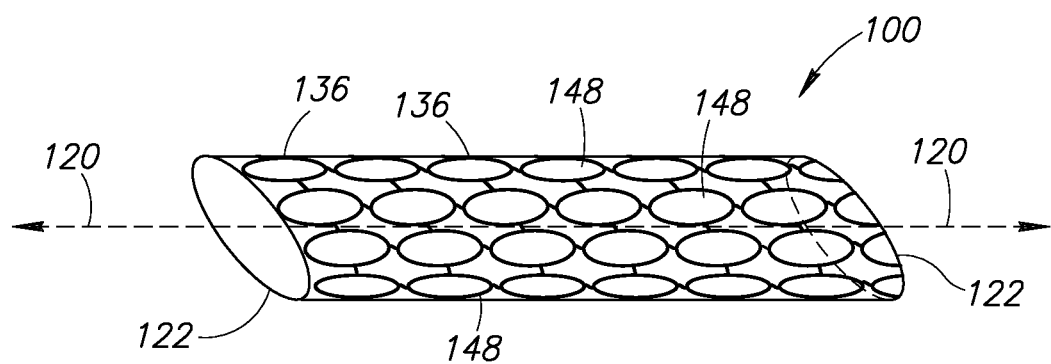
FIGS. 7A and 7B are schematic illustrations of an oblique stent, showing how the configurations of strut elements as shown in FIGS. 6A-6C may be modified in order to form oblique end.
Figure 7B:
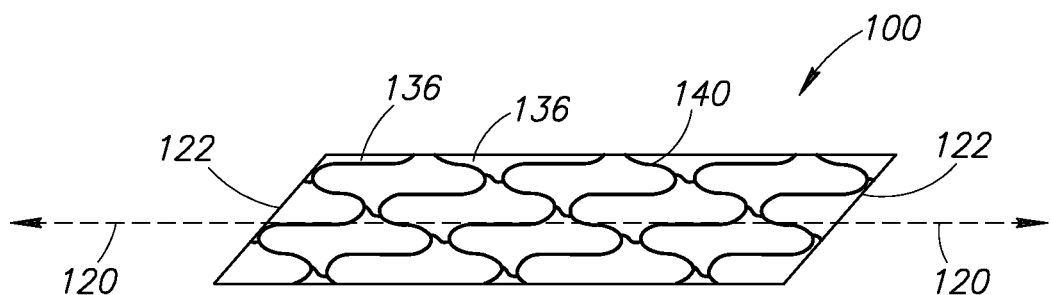

Reference is now made to FIGS. 7A and 7B, which are schematic illustrations of an oblique stent 100, showing how the configurations of strut elements as shown in FIGS. 6A-6C may be modified in order to form oblique end 122. As shown herein, circumferential rings 136 of non-oblique stent 100 are at an angle to a plane which is perpendicular to longitudinal axis 120 of oblique stent 100. In some embodiments, as shown in FIG. 7A, circumferential rings 136 may be comprised of elliptical shaped struts 148. In other embodiments, as shown in FIG. 7B, circumferential rings 136 may be comprised of axially sinusoidal strut elements 140. It should be readily apparent that circumferential rings 136 may have any configuration suitable for a stent wall and for being positioned at an oblique angle to form oblique end 122. One or both ends of oblique stent 100 may be oblique ends. To form a truncated oblique stent 300, a long edge of oblique end 122 may be cut, as described above with reference to FIGS. 5A and 5B.

Figure 8:
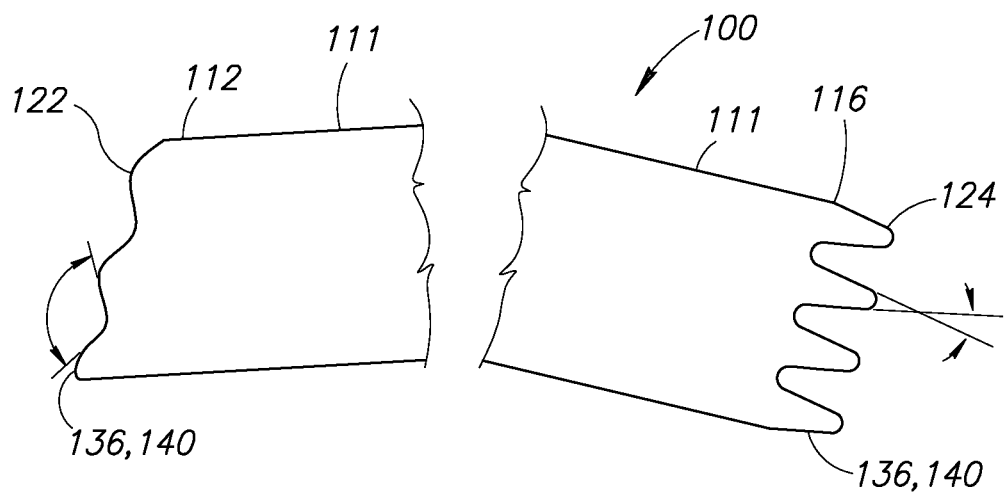
FIG. 8 is a schematic illustration of an oblique stent wherein a proximal end is an oblique end and a distal end is a perpendicular end.

Reference is now made to FIG. 8, which is a schematic illustration of an oblique stent 100 wherein a distal end 112 is an oblique end 122 and a proximal end 116 is a perpendicular end 124. In the embodiment shown in FIG. 8, circumferential rings 136 are comprised of axially sinusoidal strut elements 140, wherein upon expansion of stent body 111, axially sinusoidal strut elements 140 expand into an oblique position at oblique end 122 and into a perpendicular position at perpendicular end 124. This can be accomplished by providing a very specific stent architecture, as described with reference to FIGS. 9A and 9B, for example.

Figure 9A:
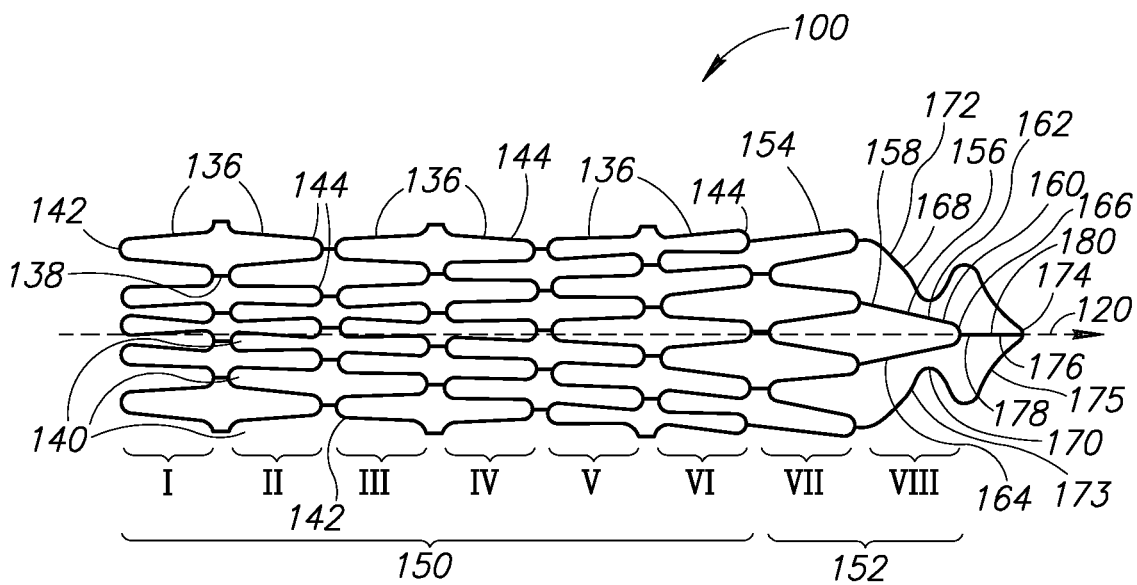
FIGS. 9A and 9B are plan view illustrations of an oblique stent, shown with stent body cut lengthwise and unrolled in an un-expanded and an expanded state, respectively.
Figure 9B:
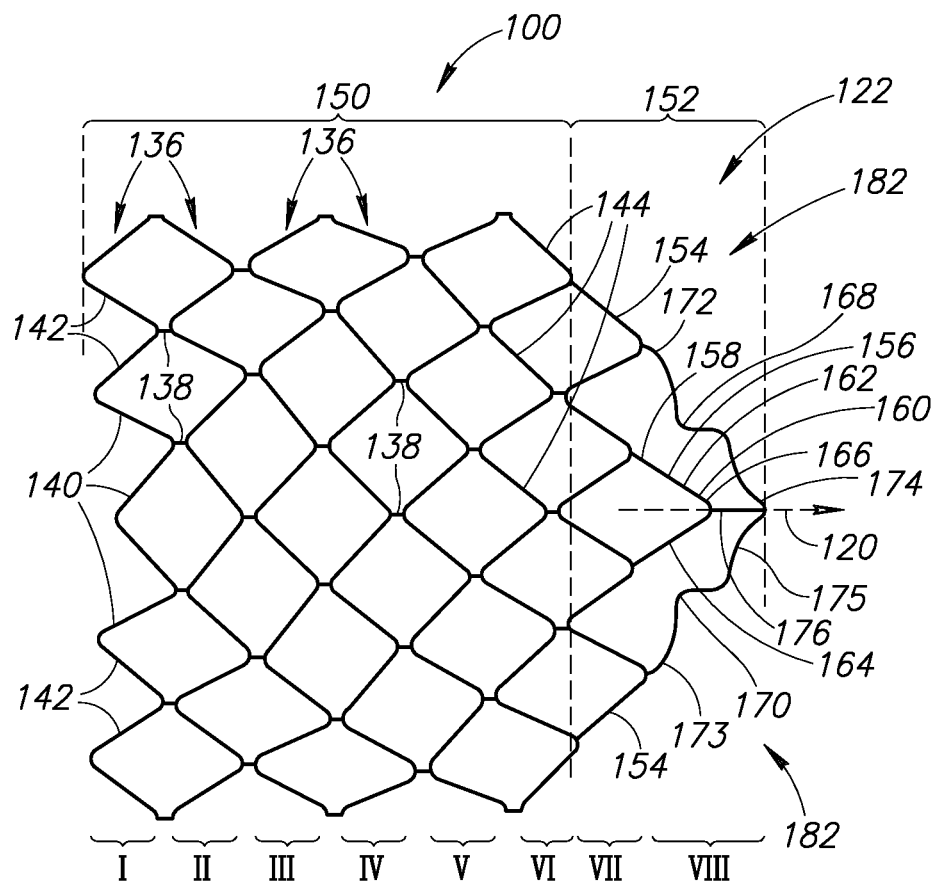

Reference is now made to FIGS. 9A and 9B, which are plan view illustrations of an oblique stent 100, shown with stent body cut lengthwise and unrolled in an un-expanded and an expanded state, respectively. As shown in FIG. 9A, oblique stent 100 is comprised of multiple adjacent circumferential rings 136, wherein each of circumferential rings 136 is connected to another of circumferential rings 136 by connecting elements 138. In the embodiment shown in FIG. 9A, circumferential rings 136 are comprised of axially sinusoidal strut elements 140. Each of axially sinusoidal strut elements 140 has a series of alternating proximal peaks 142 and distal peaks 144. Connecting elements 138 connect, for example, a distal peak 144 of a first circumferential ring 136 with a proximal peak 142 of another circumferential ring 136. Each of circumferential rings 136 is depicted independently in FIG. 9A in axial zones I-VIII, wherein axial zones I-VI comprise a body section 150, and rings VII and VIII comprise an oblique end section 152, as will be described in greater detail herein below. Each of circumferential rings 136 of body section 150 is arranged perpendicular to a longitudinal axis 120 of oblique stent 100. Axial zone VII of oblique end section 152 includes a circumferential ring 136 of axially sinusoidal strut elements 140, wherein the number of axially sinusoidal strut elements 140 in axial zone VII is less than the number of axially sinusoidal strut elements 140 in axial zones I-VI. This results in a circumference of axial zone VII being smaller than a circumference of axial zones I-VI. In the embodiment shown herein, for axial zones I-VI, proximal peaks 142 of axial zone II are connected via connecting elements 138 to distal peaks 144 of axial zone I. Similarly, proximal peaks 142 of axial zone III are connected via connecting elements 138 to distal peaks of axial zone II. This pattern may continue throughout body section 150. The connections between body section 150 and oblique end section 152 are different. In this embodiment, proximal peaks 142 of axial zone VII for axially sinusoidal strut elements 140 which are in the middle are connected to distal peaks 144 of axial zone VI. Axially sinusoidal strut elements 140 on edges of axial zone VII have foot portions 154 at two ends thereof, and these foot portions 154 are connected to distal peaks 144 at the top and bottom edges of axial zone VI.

Axial zone VIII of oblique stent 100 includes a triangular central element 156 having a triangular central element proximal end 158 and a triangular central element distal end 160. Triangular central element proximal end 158 includes a first leg 162 and a second leg 164, and triangular central element distal end 160 includes an apex 166 of triangular central element 156. Axial zone VIII further comprises a first longitudinally sinusoidal strut element 168 positioned above triangular central element 156 and a second longitudinally sinusoidal strut element 170 positioned below triangular central element 156. First longitudinally sinusoidal strut element 168 has a first longitudinally sinusoidal strut element proximal end 172 and a first longitudinally sinusoidal strut element distal end 174. Second longitudinally sinusoidal strut element 170 has a second longitudinally sinusoidal strut element proximal end 173 and a second longitudinally sinusoidal strut element distal end 175. Axial zone VIII further includes a straight strut element 176 positioned distal to triangular central element 156 having a straight strut element proximal end 178 and a straight strut element distal end 180. First leg 162 and second leg 164 of triangular central element 154 are connected to two of distal peaks 144 of axially sinusoidal strut elements 140 of axial zone VII. Triangular central element distal end 160 is connected to straight strut element proximal end 178. First and second longitudinally sinusoidal strut element proximal ends 172 and 173 are connected to outer two distal peaks 144 of axially sinusoidal strut elements of axial zone VII. First and second longitudinally sinusoidal strut element distal ends 174 and 175 are connected to straight strut element distal end 180.

Stent 100 is shown in an expanded state in FIG. 9B. It should be readily apparent that in the embodiment shown herein, axially sinusoidal strut elements 140 expand in a circumferential direction, thus allowing stent 100 to expand. If connecting elements 138 are straight, as depicted in FIGS. 9A and 9B, expansion of oblique stent 100 causes foreshortening of oblique stent 100 along longitudinal axis 120. In some embodiments, connecting elements 138 are sinusoidal or s-shaped, thus precluding foreshortening of oblique stent 100 upon expansion thereof. First and second longitudinally sinusoidal strut elements 168 and 170 expand in a longitudinal/axial direction, thus turning first and second longitudinally sinusoidal strut elements into substantially straight elements. These straightened elements thus form an outer edge 182 of oblique end 122.

Figure 10A:
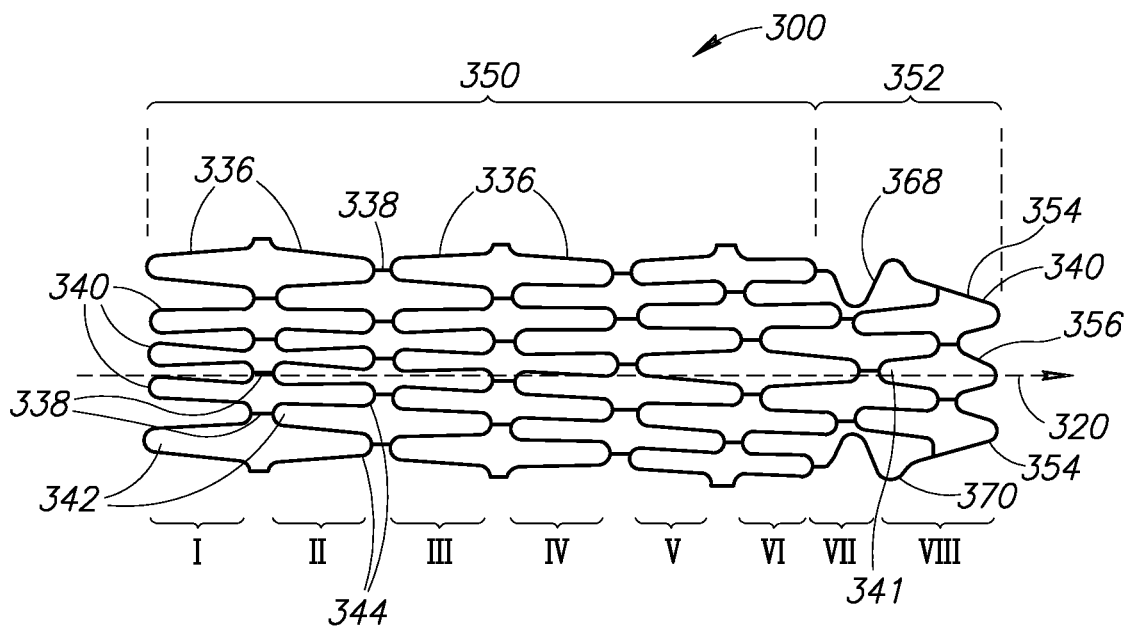
FIGS. 10A and 10B are plan view illustrations of a truncated oblique stent, shown with stent body cut lengthwise and unrolled in an un-expanded and an expanded state, respectively.
Figure 10B:
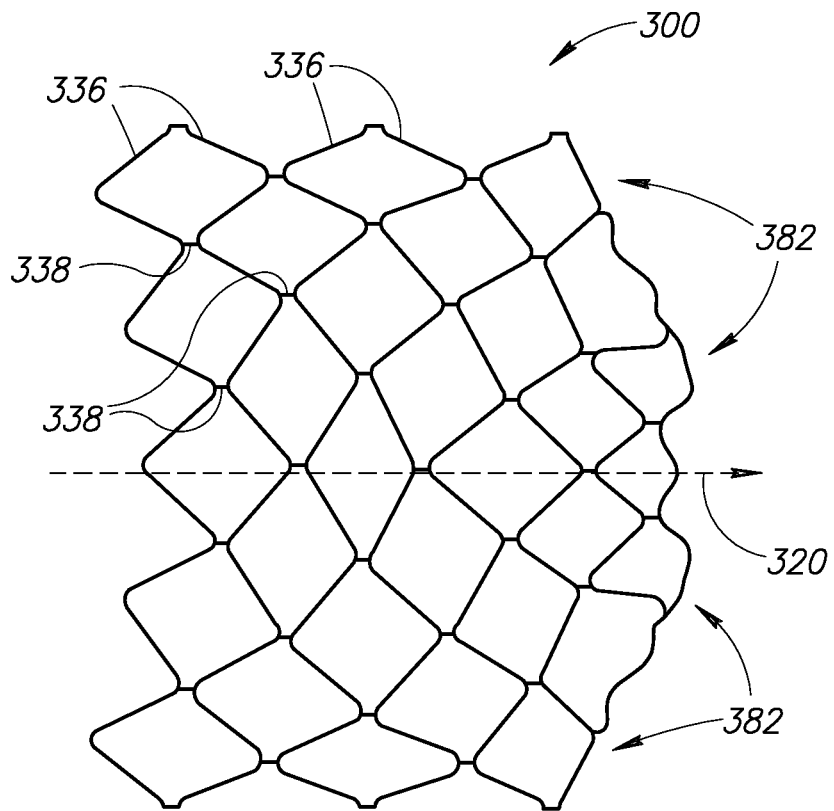

Reference is now made to FIGS. 10A and 10B, which are plan view illustrations of a truncated oblique stent 300, shown with stent body cut lengthwise and unrolled in an un-expanded and an expanded state, respectively. As shown in FIG. 10A, truncated oblique stent 300 is comprised of multiple adjacent circumferential rings 336, wherein each of circumferential rings 336 is connected to another of circumferential rings 336 by connecting elements 338. In the embodiment shown in FIG. 10A, circumferential rings 336 are comprised of axially sinusoidal strut elements 340. Each of axially sinusoidal strut elements 340 has a series of alternating proximal peaks 342 and distal peaks 344. Connecting elements 338 connect, for example, a distal peak 344 of a first circumferential ring 336 with a proximal peak 342 of another circumferential ring 336. Each of circumferential rings 336 is depicted independently in FIG. 10A in axial zones I-VIII, wherein axial zones I-VI comprise a body section 350, and rings VII and VIII comprise a truncated oblique end section 352, as will be described in greater detail herein below. Each of circumferential rings 336 of body section 350 is arranged perpendicular to a longitudinal axis 320 of truncated oblique stent 300. Axial zone VII of truncated oblique end section 352 includes a circumferential ring 336 of axially sinusoidal strut elements 340, wherein the number of axially sinusoidal strut elements 340 in axial zone VII is less than the number of axially sinusoidal strut elements 340 in axial zones I-VI. This results in a circumference of axial zone VII being smaller than a circumference of axial zones I-VI. In the embodiment shown herein, for axial zones I-VI, proximal peaks 342 of axial zone II are connected via connecting elements 338 to distal peaks 344 of axial zone I. Similarly, proximal peaks 342 of axial zone III are connected via connecting elements 338 to distal peaks of axial zone II. This pattern may continue throughout body section 350. In some embodiments, as shown in FIG. 10A, axially sinusoidal strut elements 340 of axial zones V and VI protrude slightly in a circumferential direction and in a distal direction.

The connections between body section 350 and truncated oblique end section 352 are different. In this embodiment, proximal peaks 342 of for axially sinusoidal strut elements which are in a middle of axial zone VII are connected to distal peaks 344 of axial zone VI. A central axially sinusoidal strut element 341 is slightly shorter in a longitudinal direction than other axially sinusoidal strut elements 340. A first longitudinally sinusoidal outer edge strut 368 is positioned above axially longitudinal strut elements 340 of axial zone VII, and a second longitudinally sinusoidal outer edge strut 370 is positioned below axially longitudinal strut elements 340 of axial zone VII. First and second longitudinally sinusoidal strut elements 368 and 370 are connected to distal peaks 344 at the top and bottom edges of axial zone VI.

Axial zone VIII of truncated oblique stent 300 includes a terminal end piece 356 having a series of axially sinusoidal strut elements 340, wherein proximal peaks 342 of axially sinusoidal strut elements in the middle of axial zone VIII are connected to distal peaks 344 of axially sinusoidal strut elements 340 of axial zone VII. In addition, axially sinusoidal strut elements 340 on edges of axial zone VIII have leg portions 354 at two ends thereof, and these leg portions 354 are connected to longitudinally sinusoidal strut elements 368 and 370 at the top and bottom edges of axial zone VII.

Truncated oblique stent 300 is shown in an expanded state in FIG. 10B. It should be readily apparent that in the embodiment shown herein, axially sinusoidal strut elements 340 expand in a circumferential direction, thus allowing truncated oblique stent 300 to expand. If connecting elements 338 are straight, as depicted in FIGS. 10A and 10B, expansion of truncated oblique stent 300 causes foreshortening of truncated oblique stent 300 along longitudinal axis 320. In some embodiments, connecting elements 338 are sinusoidal or s-shaped, thus precluding foreshortening of truncated oblique stent 300 upon expansion thereof. First and second longitudinally sinusoidal strut elements 368 and 370 expand in a longitudinal/axial direction, thus turning first and second longitudinally sinusoidal strut elements into substantially straight elements. Moreover, axially sinusoidal strut elements 340 of axial zone VIII also turn into substantially straight elements upon expansion of truncated oblique stent 300. These straightened elements thus form an outer edge 382 of truncated oblique end 322, included a truncated outer edge at a distal end thereof. It should be readily apparent that a similar design may be used at a proximal end of truncated oblique stent 300 to form an oblique end 322 at proximal end as well.

Figure 11A:
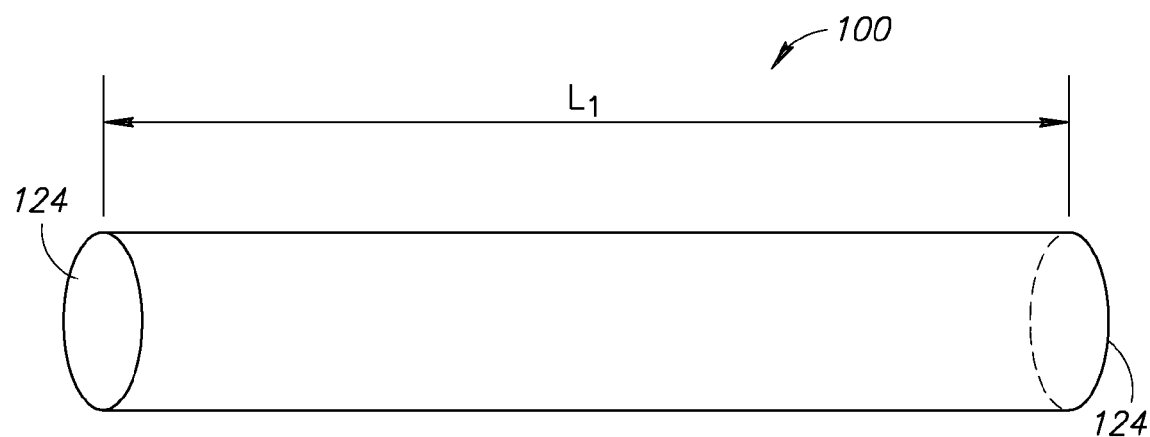
FIGS. 11A and 11B are schematic illustrations showing an oblique stent having a first configuration in an unexpanded state and a second configuration in an expanded state.
Figure 11B:
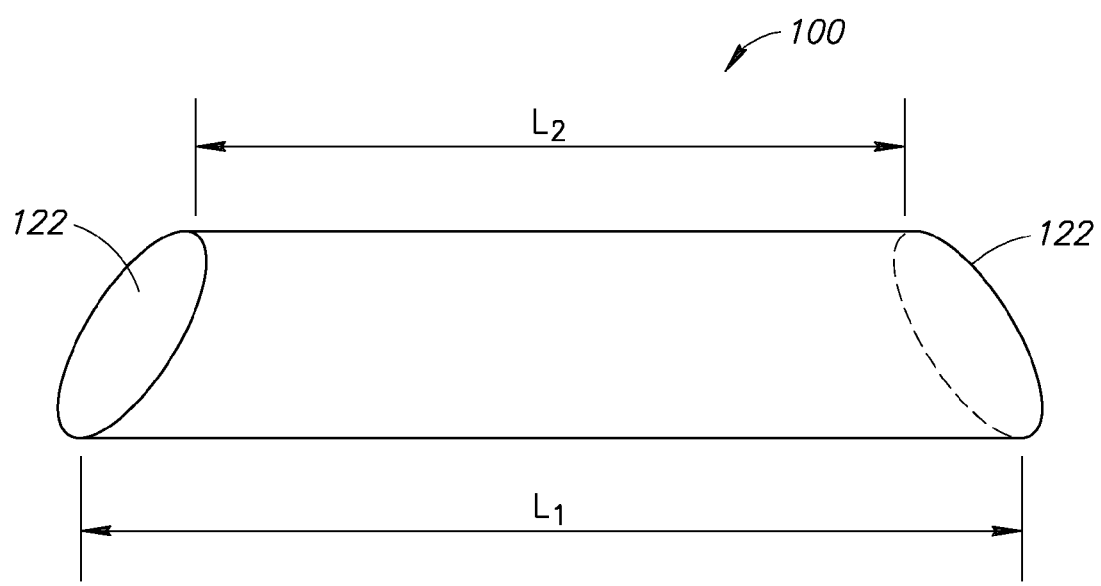

Reference is now made to FIGS. 11A and 11B, which are schematic illustrations of an oblique stent 100 having a first configuration (shown in FIG. 11A) wherein in an unexpanded state, oblique stent 100 comprises two perpendicular ends 124 and a second configuration (shown in FIG. 11B) wherein in an expanded state, oblique stent 100 comprises two oblique ends 122. In these embodiments, the unexpanded oblique stent 100 may have a length L1 at a top portion thereof and the same length L1 at a bottom portion thereof, as shown in FIG. 11A. The expanded oblique stent 100 may have a first length L1 at a bottom portion thereof and a second length L2 at a top portion thereof, or vice versa, as shown in FIG. 11B. This can be accomplished by using differential properties to foreshorten or contract longitudinally under radial expansion of differential stent wall architectures within the radial circumference/extension of such architecture.

Figure 12A:
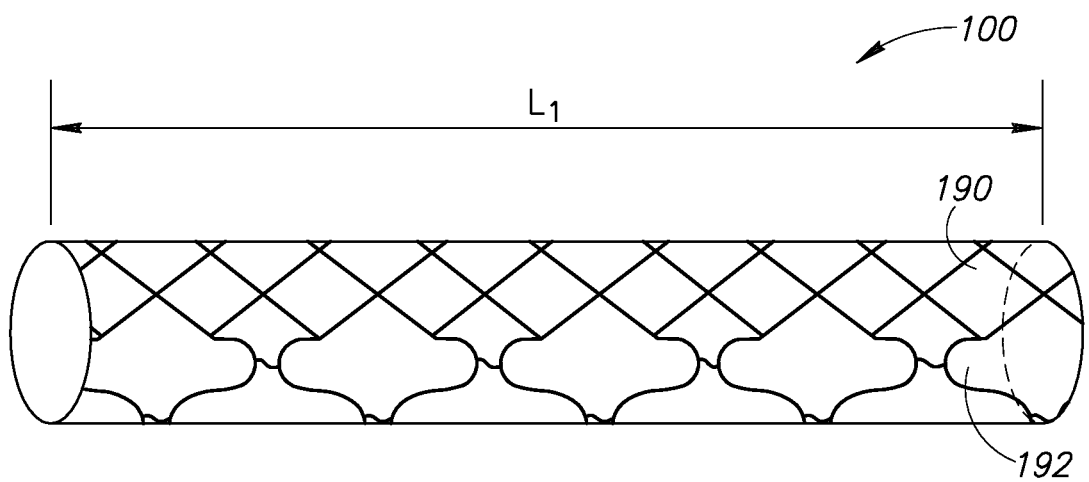
FIGS. 12A-12C are schematic illustrations of the stent of FIGS. 11A and 11B, showing a stent architecture in accordance with embodiments of the present invention.
Figure 12B:
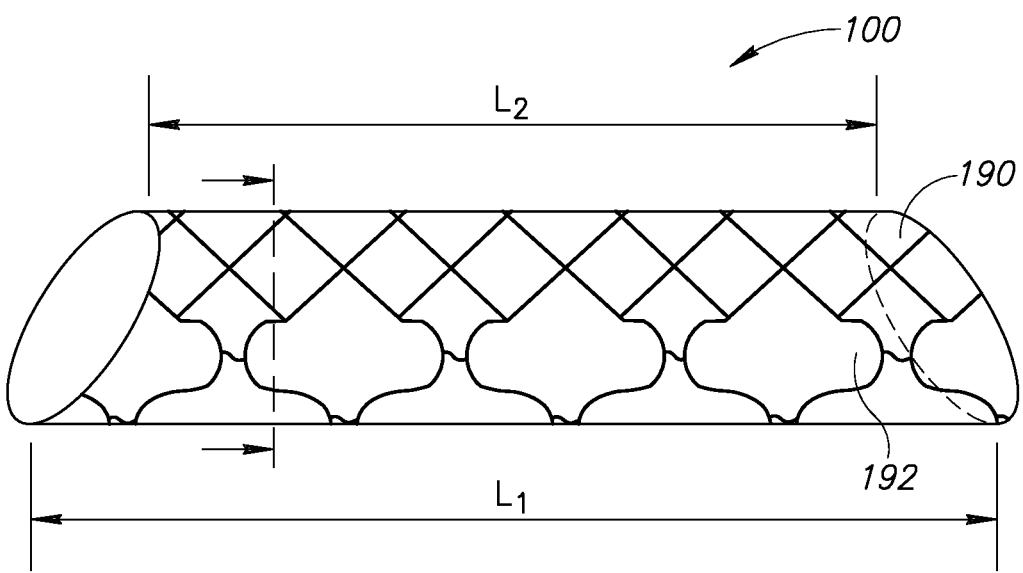
Figure 12C:
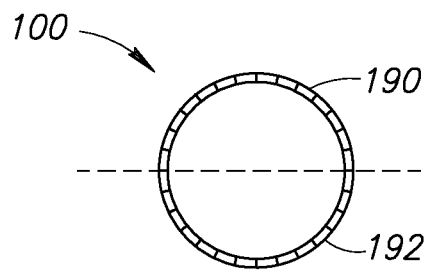

Reference is now made to FIGS. 12A-12C, which are schematic illustrations of the stent of FIGS. 11A and 11B, showing a stent architecture in accordance with embodiments of the present invention. In the embodiments shown herein, half of the circumference of oblique stent 100, for example, upper half 190 comprises a longitudinally contracting configuration, such as a diamond strut configuration. The opposing half, for example, lower half 192, is comprised of a longitudinal length-maintaining configuration having for example, sinusoidal, curved or S-shaped struts and/or connecting elements. Upper half 190 and/or lower half 192 may be portions which are less than or more than half the circumference of oblique stent 100. FIG. 12C is a cross-sectional illustration of oblique stent 100 of FIGS. 12A and 12B. It should be readily apparent that similar designs may be used for truncated oblique stents 300 as well.

Oblique stent 100 and truncated oblique stent 300 must be positioned in a vessel such that oblique end 122, 322 is positioned properly within the bifurcation. A delivery system which provides for torqueability or which permits self-positioning may be used for this purpose. Such delivery systems are known in the art. In addition, radiopaque markers may be used to identify the oblique ends of the stent, including, for example, a maker on the longest portion and another marker on the shortest portion of oblique end 122, 322. Additional markers may be used as well, including markers at other locations of the stent and/or on the delivery system. Stent 100, 300 may be balloon expandable or may be self-expanding. Self-expanding stents may be used in particular situations such as in diameters with large vessels. Stent 100, 300 may be comprised of metallic material or non-metallic materials.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A tubular stent comprising:
   a stent first end;
   a stent second end;
   a longitudinal axis extending from said stent first end to said stent second end; and
   an expandable stent wall extending from said stent first end to said stent second end along said longitudinal axis, said expandable stent wall comprising:
      a first circumferential ring connected to a second circumferential ring by a first connecting element, wherein said second circumferential ring is positioned adjacent to said first circumferential ring along said longitudinal axis; and
      at least one terminal end piece connected to said second circumferential ring and positioned at said stent first end and adjacent to said second circumferential ring, wherein upon expansion of said tubular stent, said at least one terminal end piece is configured to expand into a substantially straight element forming an outer edge of said tubular stent at said stent first end, and
   wherein upon expansion of said tubular stent, said stent first end is configured at an oblique angle to a plane which is perpendicular to said longitudinal axis.

2. The tubular stent of claim 1, wherein said stent second end is configured parallel to a plane which is perpendicular to said longitudinal axis.

3. The tubular stent of claim 1, wherein said stent first end is a truncated oblique end.

4. The tubular stent of claim 3, wherein stent first end includes a portion which is cut at an angle to a plane which is perpendicular to said longitudinal axis, and further includes a truncated portion which is cut parallel to a plane which is perpendicular to said longitudinal axis.

5. The tubular stent of claim 1, wherein said expandable stent wall is comprised of an architecture which in an unexpanded configuration is non-oblique and in an expanded configuration comprises at least one oblique end.

6. The tubular stent of claim 1, wherein said expandable stent wall includes a body portion having body portion strut elements and an end section having end section strut elements, wherein said end section strut elements have a different configuration than said body portion strut elements.

7. The tubular stent of claim 6, wherein said body portion strut elements are circumferentially arranged axially sinusoidal strut elements comprising proximal and distal peaks in a direction of said longitudinal axis, said axially sinusoidal strut elements forming neighboring circumferential rings, wherein a first circumferential ring is connected to a second circumferential ring via connecting elements attaching said distal peaks of said first circumferential ring to said proximal peaks of said second circumferential rings.

8. The tubular stent of claim 6, wherein said end section comprises:
   a first longitudinally sinusoidal outer edge strut;
   a second longitudinally sinusoidal outer edge strut; and
   an axially sinusoidal element comprising sinusoidal element proximal peaks and sinusoidal element distal peaks, said axially sinusoidal element sandwiched between said first and second longitudinally sinusoidal outer edge struts, wherein said terminal end piece is a terminal axially sinusoidal end piece comprising:
   multiple sinusoidal portions having a shorter amplitude than an amplitude of said axially sinusoidal elements;
   terminal end piece distal peaks and terminal end piece proximal peaks on said multiple sinusoidal portions; and
   an end piece top left leg and an end piece bottom left leg, wherein said sinusoidal element distal peaks are connected to said terminal end piece proximal peaks, and wherein said first longitudinally sinusoidal outer edge element is connected to said end piece top left leg and said second longitudinally sinusoidal outer edge element is connected to said end piece bottom left leg.

9. The tubular stent of claim 7, wherein said connecting elements are straight connecting elements.

10. The tubular stent of claim 6, wherein a number of said end section strut elements is smaller than a number of said body section strut elements.

11. The tubular stent of claim 1, wherein said at least one terminal end piece comprises axially sinusoidal strut elements.

* * * * *